(12) United States Patent
Beydoun et al.

(10) Patent No.: US 10,839,956 B2
(45) Date of Patent: Nov. 17, 2020

(54) UNIVERSAL DEVICE AND METHOD TO INTEGRATE DIAGNOSTIC TESTING INTO TREATMENT IN REAL-TIME

(71) Applicant: University of Maryland Medical Center, Baltimore, MD (US)

(72) Inventors: Alaa Beydoun, Baltimore, MD (US); Vikash Gupta, Baltimore, MD (US)

(73) Assignee: University of Maryland Medical Center, Baltimore, MD (US)

( * ) Notice: Subject to any disclaimer, the term of this patent is extended or adjusted under 35 U.S.C. 154(b) by 185 days.

(21) Appl. No.: 15/910,155

(22) Filed: Mar. 2, 2018

(65) Prior Publication Data

US 2018/0254099 A1 Sep. 6, 2018

Related U.S. Application Data

(60) Provisional application No. 62/466,689, filed on Mar. 3, 2017.

(51) Int. Cl.
*G06K 9/00* (2006.01)
*G16H 30/40* (2018.01)
(Continued)

(52) U.S. Cl.
CPC ........... *G16H 30/40* (2018.01); *A61B 90/361* (2016.02); *A61B 90/37* (2016.02); *A61B 90/53* (2016.02); *G06T 7/0012* (2013.01); *G06T 7/246* (2017.01); *G06T 11/60* (2013.01); *G16H 10/60* (2018.01); *G16H 40/63* (2018.01); *G16H 50/20* (2018.01); *A61B 2017/00203* (2013.01); *A61B 2017/00207* (2013.01); *A61B 2017/00216* (2013.01); *A61B 2034/2048* (2016.02);
(Continued)

(58) Field of Classification Search
CPC ........ A61B 2090/363; A61B 2090/366; A61B 2090/374; A61B 2090/3762; A61B 2090/378; A61B 2090/502; A61B 2560/0247; A61B 90/37; A61B 90/53; A61B 2090/372; G06T 11/60; G06T 2207/10072; G06T 9/00; G06T 2207/10016; G06T 2207/10081; G06T 2207/30204; G06T 7/246; G16H 10/60; G16H 30/40; G16H 40/63; G16H 50/20
See application file for complete search history.

(56) References Cited

U.S. PATENT DOCUMENTS

6,493,575 B1 * 12/2002 Kesten ................... A61B 90/36
600/431
8,696,121 B1 * 4/2014 Fram ....................... G06F 3/013
351/200
(Continued)

*Primary Examiner* — Li Liu
(74) *Attorney, Agent, or Firm* — Miles & Stockbridge P.C.

(57) ABSTRACT

A method and system for integrated diagnostic testing and real-time treatment that includes a medical data gathering device to capture multiple of source images, where at least one of the source images contains a fiducial marker. The method and system incorporate a low latency encoder to encode the captured source images into a data stream and further includes an environmental sensor device for the capturing of sensor data. A processor is used to contextually modify the source images based on the captured sensor data and the fiducial marker and a transmitting device is used to transmit the contextually modified source images to a display device.

20 Claims, 8 Drawing Sheets (51) Int. Cl.
*G06T 7/00* (2017.01)
*G06T 11/60* (2006.01)
*A61B 90/00* (2016.01)
*A61B 90/53* (2016.01)
*G16H 10/60* (2018.01)
*G16H 50/20* (2018.01)
*G06T 7/246* (2017.01)
*G16H 40/63* (2018.01)
*G06T 9/00* (2006.01)
*A61B 90/50* (2016.01)
*A61B 17/00* (2006.01)
*A61B 34/20* (2016.01)

(52) U.S. Cl.
CPC .......... *A61B 2034/2051* (2016.02); *A61B 2090/363* (2016.02); *A61B 2090/365* (2016.02); *A61B 2090/366* (2016.02); *A61B 2090/372* (2016.02); *A61B 2090/374* (2016.02); *A61B 2090/378* (2016.02); *A61B 2090/3762* (2016.02); *A61B 2090/502* (2016.02); *A61B 2560/0247* (2013.01); *A61B 2560/0493* (2013.01); *G06T 9/00* (2013.01); *G06T 2207/10016* (2013.01); *G06T 2207/10072* (2013.01); *G06T 2207/10081* (2013.01); *G06T 2207/30044* (2013.01); *G06T 2207/30204* (2013.01)

(56) References Cited

U.S. PATENT DOCUMENTS

| | | | | |
|---|---|---|---|---|
| 10,206,661 | B2* | 2/2019 | Mammone | A61B 8/5223 |
| 2008/0033240 | A1* | 2/2008 | Hoffman | A61B 90/36 |
| | | | | 600/109 |
| 2008/0243142 | A1* | 10/2008 | Gildenberg | G16H 50/50 |
| | | | | 606/130 |
| 2009/0171184 | A1* | 7/2009 | Jenkins | A61B 5/7435 |
| | | | | 600/411 |
| 2011/0210261 | A1* | 9/2011 | Maurer, Jr. | A61N 5/10 |
| | | | | 250/393 |
| 2012/0143029 | A1 | 6/2012 | Silverstein et al. | |
| 2015/0035942 | A1* | 2/2015 | Hampton | G06T 19/00 |
| | | | | 348/42 |
| 2015/0073259 | A1* | 3/2015 | Zhou | G01R 33/285 |
| | | | | 600/411 |
| 2015/0173715 | A1 | 6/2015 | Raghavan et al. | |
| 2016/0035108 | A1 | 2/2016 | Yu et al. | |
| 2016/0338676 | A1 | 11/2016 | Berger et al. | |
| 2018/0168732 | A1* | 6/2018 | Trousset | A61B 34/20 |
| 2018/0185100 | A1* | 7/2018 | Weinstein | A61B 34/20 |
| 2018/0185113 | A1* | 7/2018 | Gregerson | A61B 34/20 |
| 2019/0090976 | A1* | 3/2019 | Wade | G06F 3/0481 |

\* cited by examiner

UNIVERSAL DEVICE AND METHOD TO INTEGRATE DIAGNOSTIC TESTING INTO TREATMENT IN REAL-TIME

CROSS REFERENCE TO RELATED APPLICATIONS

This application is a non-provisional application that claims the benefit of U.S. provisional Application No. 62/466,689, filed on Mar. 3, 2017, the contents of which are herein incorporated by reference in their entirety.

FIELD OF THE INVENTION

The embodiments of the present invention generally relate to improvements in technology related to medical diagnoses and treatments, and more particularly, to medical imaging devices.

BACKGROUND OF THE INVENTION

In the course of assisting patients, medical professionals rely on a variety of devices to assist with diagnosing and treating a variety of ailments and illnesses that affect patients. Medical equipment, in the modern healthcare environment, includes devices that allow for the measurement of biological parameters that can be interpreted by healthcare providers to direct patient care. Such biological parameters may include vital signs such as blood pressure and heart rate, images of the body and its structures, and various other biological parameters that may be stored on a centralized database known as an electronic medical record (EMR).

Typically, a patient seeking medical advice may first undergo diagnostic testing to gather information relating to various biological parameters or to generate images of the patient that are then passed on to a nurse, technologist, or physician for review prior to any treatment. The images generated during diagnostic testing are used to assist the medical professionals in deciding on a course of treatment, including specific procedures to help alleviate or repair whatever pain or injury that is bothering the patient. Examples of diagnostic testing may include radiology, nuclear medicine, ultrasound, and other image generating techniques. Additionally, biological parameters and images may be provided concurrently with services provided during treatment via directly connected display monitors and physical printouts.

SUMMARY OF THE INVENTION

Accordingly, the embodiments of the present invention are directed to systems and methods that integrate diagnostic testing into treatment in real-time, i.e., real-time treatment, that substantially obviate one or more problems due to limitations and disadvantages of the related art.

Systems and methods are provided to assist with providing contextually-appropriate displays of data in real-time to a user such as a medical professional. The contextually-appropriate displays of data may be presented as biometric information and diagnostic and other images. The data is collected and processed such that environmental information is considered in the presentation of the data to the medical professional such that the display of the data is appropriate for the particular setting in which the data is being collected.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the integrated diagnostic testing and treatment in real-time, i.e., real-time treatment, includes each of a method, system, device, and computer readable medium configured for visualizing data in real-time, including collecting data, transmitting data to a data transformation device, sensing a first environment in which the data is collected, sensing a second environment in which the data is to be displayed, transforming the data contextually based on at least the second environment, transmitting the contextually modified data to a data display device, and displaying the contextually modified data.

Further, additional advantages may be provided by digitally mapping the environment and tracking regions while displaying contextually modified data in anatomically accurate overlays, the overlays embodied as being generated via fiducial and other trackable markers which may be in sterile operative and procedural fields.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION

The embodiments of the present invention are generally directed toward systems and methods that enable a device to connect to any medical data gathering device or imaging device, analog or digital, and that allow for near real-time encoding using a low latency encoder and streaming of captured data and images, e.g., a data stream of images. The medical gathering device can be any type of medical instrument or medical tool or device. The embodiments may include a device that connects to any video output port or another connection port of a medical imaging device. The embodiments may include coding and processes to provide contextually-appropriate images from the medical imaging device to a medical professional in real-time, preferably during a medical procedure.

The present invention may embody a device that may be linked to standard data capturing equipment used in modern medicine through standard ports, wireless connections, or optical sensors. The device may have the capability of capturing relevant data from such equipment and, in a low-latency process, wirelessly transmit this modified or unmodified data over various protocols including, but not limited to, Wi-Fi standards, Bluetooth, 4G, or 5G. Low-latency means less than 250 ms, as measured between data capture and display on the target display device. For example, the embodiments are generally directed to systems and methods that may stream data, which may be images, wirelessly over a closed local network, e.g., Wi-Fi, Bluetooth, etc., or remotely. The device is designed to be universal for at least a variety of medical imaging devices and would allow for interpretation of images within as well as away from the immediate vicinity of the imaging device being used.

Additionally, the device is able to stream images to a wearable display, e.g., a Google Glass or Microsoft Hololens, allowing streaming of any medical imaging or other data without requiring a traditional display.

This device includes the ability to process data with various microprocessors including CPUs (central processing unit), GPUs (graphics processing unit), and/or custom ASICs (application specific integrated circuit). The processing capacity allows for low latency hardware based video encoding, i.e., a low latency encoder, file transcoding, cryptographic encoding, and three-dimensional modifications. The device also includes a wireless access point whereby this data can be transmitted over a secure connection such as WPA2, WPA, or other encoding algorithms.

Moreover, the device may be configured as a relay to control the imaging equipment to which it is connected. The device may be configured to respond to, for example, voice and other commands provided to the wearable display, and an application program interfaces (API) is run on the universal device, the API controlling data collection or imaging settings on the imaging equipment to which the device is connected. In other words, the device or system may include an updatable library of commands that may be transmitted to a medical device, i.e., a diagnostic tool or imaging device, from which data is being captured. These commands may be configured to allow for the wireless control of connected equipment through available APIs.

Another embodiment of the system may have the ability to receive commands and/or other data points from wearable devices or various other sensor systems that can be utilized to both control the connected equipment through the API as well as to modify the captured data prior to transmission to the wearable unit. For example, this may allow for three-dimensional manipulations of captured imaging data, such as ultrasound or computer tomography (CT) images, which can be displayed in anatomically correct locations directly on a patient during image acquisition giving the impression of viewing "into" the patient, e.g., noninvasive imagery. The system may also allow the overlay of physiological or image data with real-time viewing of the patient during a consultation, treatment, or procedure, thus providing contextual modification of the source images, also known as medical source images, performed in real-time.

A fiducial marker is an object placed in the field of view of an imaging system which appears in the image produced. This marker may be used as a point of reference or a measure. In an embodiment, a fiducial marker may be used to track a particular region on a patient allowing for source equipment data to be contextually modified based on a correlation of the fiducial marker to external sensor data such as optical sensors.

In an embodiment, a patient undergoing a diagnostic imaging scan may receive a scan with fiducial markers in place, as such these fiducial markers may be represented in the imaged data. In an embodiment, these markers may also be detected by external sensors and tracked using one or several methods including optical, laser, infrared, magnetic, or other properties. The external sensor data and source equipment data may then be correlated to one another using image modification algorithms executed by a process, thus allowing for contextual modification of the source images. Additionally, the environmental sensor data, captured by an environmental sensor device, may track the fiducial marker in real-time allowing for real-time contextual modification of source images based on the captured sensor data from the environmental sensor device, e.g., captured environmental sensor data.

In an embodiment, fiducial markers may be inherent features of the scanned object such as a contour or landmark, a unique overlay texture such as clothing or a drape, a unique shape or pattern such as an optical pattern, light source, magnetic field source, or other detectable object. In such a manner, a fiducial marker may be passive or active in structure and/or function. In an embodiment, a fiducial marker may represent a single trackable point, in another embodiment a fiducial marker may convey one or more vectors allowing it to be tracked in multiple dimensions. Additionally, in an embodiment, a fiducial marker may represent an initial marker source whereby environmental sensor devices may map adjacent environmental features, structures, and textures to extend the characteristics, size, and accuracy of the tracked fiducial marker.

In the context of image guided medical procedures, a fiducial marker may need to be included in source data prior to field sterilization yet also visible and accessible to environmental tracking equipment after field sterilization. Additionally, the fiducial marker may need to be overlaid on a sterile surgical field/drape and remain fixed in position relative to the subject while being tracked. In this manner, a fiducial marker may need to both be present before and after sterilization of the surgical field, be included in the sterile field without compromising sterility, and not change its position before and after the process of surgical field sterilization.

In an embodiment, self-aligning and complementarily-attracting fiducial markers may be used to address these essential components of accurate environmental tracking during image guided procedures. In such an embodiment, an adhesive or non-adhesive based fiducial marker may be affixed to a specific site of an imaged subject during initial data acquisition. This fiducial marker may remain in unchanged position during site sterilization and covered during placement of a sterile surgical drape. Subsequently, a complementary sterile fiducial marker may be attached to the initial marker through the drape using attractive forces such as through magnetic or electronic force attraction. These two fiducial markers, when brought close to one another, may self-align based on their fundamental properties and the over-drape fiducial marker may be tracked by the environmental sensor equipment, acting as an accurate surrogate of the non-sterile marker. In an embodiment, the surrounding drape configuration and texture may also be mapped to expand the trackable region. In other embodiments, multiple fiducial markers may be used, a non-sterile marker may be sterilized, environmental sensor equipment may be able to track a covered marker, or marker sites may be accurately defined after sterilization In another embodiment, additional trackable markers may be placed to extend the trackable region. The relationship of these additional markers to the initially placed markers may be extrapolated to extend the trackable field and/or provide additional fiducial points for contextual image modification. In this manner, additional trackable points may be used should the originally placed fiducial marker or markers not be sufficiently trackable by environmental sensors.

From the data capturing device, the capture data encoding may be hardware accelerated to minimize latency. Low latency is important for providing real-time interpretation of images taken by the data source equipment, e.g., source images. The device is designed robustly such that the device may be adapted to utilize in any ultra-low-latency streaming application, in particular over a wireless network.

The embodiments may be applied to a variety of medical technologies, including, for example, diagnostic radiology, interventional radiology, imaged guided surgery, nuclear medicine, ultrasound, sonography, etc. Diagnostic radiology is concerned with the use of various imaging modalities to aid in the diagnosis of disease. Diagnostic radiology may use x-ray machines, other radiation devices, and techniques such as magnetic resonance imaging (MRI) and ultrasound that may not involve radiation. Interventional radiology is concerned with using medical image data to guide medical interventions and procedures using tools such as catheters, wires, coils, probes, or other appropriate equipment.

Nuclear medicine is a medical specialty involving the application of radioactive substances in the diagnosis and treatment of disease. The radioactive substances function as tracers to help diagnose and treat a variety of diseases. Nuclear medicine involves recording radiation emitting from within the body rather than radiation generated by external sources. Nuclear medicine allows for the determination of causes of medical problems based on the function of an organ, tissue, or bone, whereas an x-ray, ultrasound, or other diagnostic test determines the presence of disease based on structural appearance.

Ultrasound, or sonography, involves the use of sound waves to view inside of a body, including internal structures. Ultrasound is most often used for viewing swelling and infection in the body's internal organs, to examine a baby in a pregnant woman, and to help with guiding biopsies, diagnose heart conditions, and assess damage after a heart attack.

Among the devices used to assist medical professionals with their professional tasks, imaging devices are becoming more important and used to provide information about patients' anatomy and physiology deep to their external skin. In other words, imaging devices allow physicians and other medical professionals to view into a patient without requiring invasive surgery.

As discussed above, healthcare information collected from a patient, in addition to being stored as an EMR, may be printed out or displayed on monitors that are wired and directly connected to these data collection devices. For the information to be useful to a medical professional, i.e., to interpret this information, there must be a direct line of sight between the healthcare provider and the printout or display monitor. Such a requirement may limit the usefulness of the information and the placement of devices for diagnostic or treatment services. In many healthcare environments, providers may have to constantly change their field of focus and adjust their line of sight in order to view all relevant information needed to direct care. Such a requirement may be cumbersome or potentially unsafe, as in the case of information collected during ongoing surgical procedures.

In some cases, medical equipment is only useful if the data collected is immediately available. For example, when performing ultrasound guided procedures whereby the operator targets biopsy of a lesion inside a patient, the operator must know the location of the tip of their needle or biopsy device at all times to ensure vital structures are not injured. As such, an essential element for real-time interpretation of this data is real-time availability to the operator.

The embodiments of the present invention are generally directed to a device, method, and system linked to standard data source equipment. Standard data source equipment includes, but is not limited to, medical equipment such as ultrasound, angiographic, fluoroscopic, fiber optic, computer tomographic, and magnetic resonance imaging machines. Embodiments of the present invention include a device configured to interact with data source equipment such as medical equipment through standard ports physically attached to the source equipment, wireless connections, and optical sensors. Standard ports may include, but are not limited to, USB, HDMI, DVI, Display port, VGA, component, composite, and S-Video ports. Standard data output ports on data source equipment may be directly connected to an embodiment, the embodiment being configured to capture data from analog and digital sources and, with low latency (i.e., <250 ms), wirelessly transmit data, either in an original form or a modified, e.g., encrypted, form. Transmission of the data may be over a wireless protocol, including Wi-Fi standards such as 802.11a, 802.11b, 802.11n, 802.11ac, and 802.11ad, Bluetooth, and 4G or 5G networks. Transmission of the data may be performed using packet switching protocols, e.g., a User Data Protocol (UDP) or a Transmission Control Protocol (TCP).

In an embodiment, the system may include computer vision and/or optical character recognition (OCR) algorithms allowing for data mining of captured data from source equipment. For example, when capturing from an ultrasound machine, the system may extract data points embedded within the captured source images such as a patient's name, other identifying information, image acquisition parameters, and/or other text overlay information.

An embodiment of the device provides transmission of data with low latency. Low latency is considered approximately to be less than 250 ms as measured from data capture to display on a target display device. Low latency is an important aspect of the application, as a medical professional may need near real-time data to be able to provide safe and effective treatment. To ensure low latency capture and transmission of this data, this device/system includes micro-processing capabilities through at least the use of a CPU (central processing unit), GPU (graphics processing unit), and/or various ASIC (application specific integrated circuit) components. These components are configured to work together to provide low latency hardware encoding and/or transcoding of data prior to transmission over a secured wireless connection. Additionally, through the use of GPU and/or ASIC systems, acquired data may be modified to be displayed in various formats based on input from various environmental sensors.

To transmit this data, the system may include a wireless access point which facilitates transmission of data wirelessly over a secured connection using protocols such as WPA, WPA2, or other encoding algorithms. The data may be transmitted while the device is on a local area network (LAN) or on a wide area network (WAN). A LAN system may be preferable for transmission of highly sensitive information, e.g., private health information (PHI), since the encoded data would not be transmitted beyond the range of the access point. Additionally, a WAN system may be utilized for remote transmission of data via the internet and may facilitate a wide range of tele-presence or tele-medicine capabilities. Aside from WiFi protocols, additional wireless streaming solutions may include other radio-based wireless transmission protocols such as those defined by the Bluetooth standard or other potential protocols.

Additionally, in an embodiment, the system may include a library of commands which may be transmitted to the equipment from which data is captured. The library may be updated via wireless connections to the internet or using patches locally executed on the device. The system may be configured to automatically detect a type of source data source being transferred. The system may also be configured to select an appropriate API from the library based on the type of source data being transferred. In an embodiment, manual selection of an appropriate API may be performed instead or in addition to the automatic selection.

The libraries are configured to allow for wireless control of connected equipment through available specific application programming integrations (API). For example, in an exemplary embodiment, a user may submit any number of commands to the system using a voice command, physical gesture, or other appropriate method. The command, in turn, may be interpreted by the system and relayed to the device from which data is being captured. The command in turn causes the system to alter the data acquisition parameters as intended by the user.

In an embodiment, third party devices communicate with the system using an API system. The API system, which may be customizable for the third party devices based on device type, brand, file type or other parameters, allows for transmission and utilization of various commands and/or environmental parameters including, but not limited to, input commands (such as voice, gesture, eye tracking, keyboard, mouse, or trackpad) and environmental sensor data, e.g., captured sensor data (such as those acquired by gyro-sensors, accelerometers, laser positioning systems, magnetometers, and/or optical cameras). Commands may be configured to allow for control of the system and/or data source equipment. Additionally, environmental sensor data may be integrated and interpreted by the system to modify source data contextually. Contextual modifications may be made by the system prior to transmission. Transmitted data, sent by a transmitting device, may then be sent to a wearable unit or otherwise displayed to a user, such as a medical professional.

For example, in an exemplary implementation, a user would utilize a wearable display device that includes sensors such as cameras, eye trackers, and/or positional sensors while using an ultrasound source device to target biopsy of a mass within a patient's liver using a needle biopsy device. In this example, the ultrasound source machine would be connected to the system over a wired connection allowing the system to capture images from the ultrasound machine. The system would be wirelessly connected to a wearable display device over a secure connection allowing for HIPAA (Health Insurance Portability and Accountability Act) compliant low-latency transmission of captured ultrasound images to the wearable device. Additionally, the system may modify the captured ultrasound source data three-dimensionally based on environmental sensor data from the wearable device. The three-dimensional modification of the source data would then create a low-latency projection of images directly on the patient with anatomic accuracy while also projecting the path of the biopsy device. In the alternative, the low-latency transmission may be visible using the wearable device rather than projecting onto the patient. Additionally, through voice commands and gesture controls, the system may be configured to allow the user to wirelessly change acquisition parameters of the ultrasound source device without needing to physically press buttons on its console.

Figure 1:
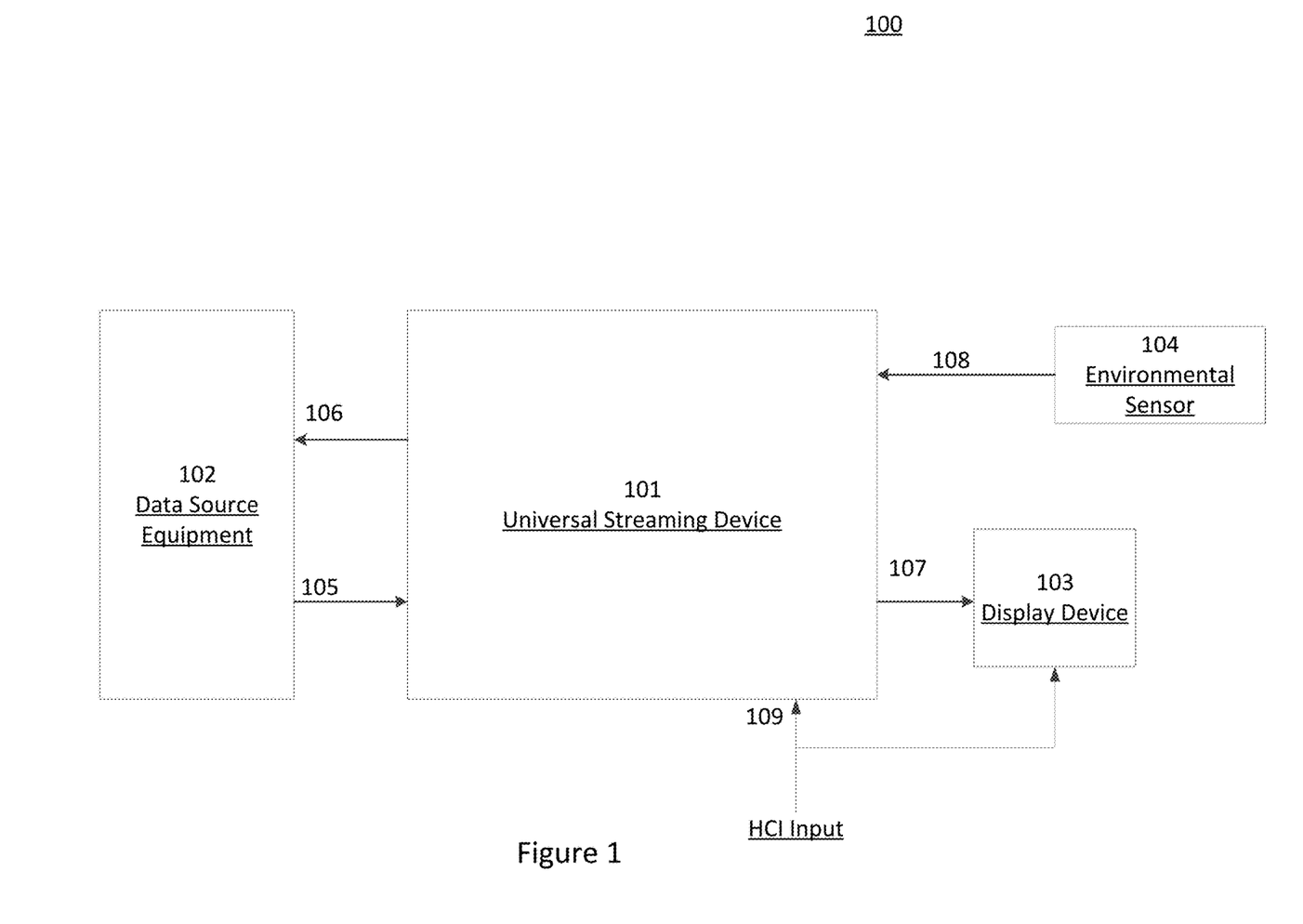
FIG. 1 illustrates a flowchart of connections to a universal streaming device according to an example embodiment.

FIG. 1 illustrates a flowchart of connections to a universal streaming device according to an example embodiment.

As shown in FIG. 1, a flow diagram of a system 100 is depicted according to an example embodiment. System 100 may include computer components including a bus and/or other communication mechanism(s) configured to communicate information between the various components of system 100, such as a processor and a memory. In addition, a communication device may enable connectivity between the processor and other devices by encoding data to be sent from the processor to another device over a network (not shown) and decoding data received from another system over the network for processor.

System 100 may include connections to a universal streaming device 101 according to an embodiment. Data source equipment 102 is configured to gather data, e.g., from a patient. Data source equipment 102 may include a port 105 via which a universal streaming device 101 according to an embodiment may be connected to data source equipment 102. The port 105 may be a USB, HDMI, DVI, Displayport, VGA, component, composite, S-Video, or other input/output port.

In an embodiment, data source equipment 102 may be physically connected to universal streaming device 101. In an alternate embodiment, data source equipment 102 may be wirelessly connected to universal streaming device 101. System 100 may also include a display device 103 upon which the data collected by data source equipment 102 may be displayed. Display device 103 may be physically connected to universal streaming device 101 in an embodiment. In another embodiment, display device 103 may be wirelessly connected to universal streaming device 101. Connection 107 between universal streaming device 101 and display device 103, which could be wearable and may be wired or unwired.

Display device 103 may be a display monitor configured to display biometric or other data or images assembled from the collected data. In an embodiment, the display device may be a wearable device displaying data or images generated from the data. The display device may also be a plurality of devices presenting data or images assembled from the data. Display device 103 may be configured to display the data or the images assembled from the data in two dimensions, in three dimensions, as a wire frame, or as an overlay over a patient. Display device 103 may be configured to integrate preexisting data or images, such as from patient records.

In an embodiment, display device 103 may also integrate information from at least an environmental sensor 104. Environmental sensor 104 may be a gyro-sensor, an accelerometer, a laser positioning system, a magnetometer, an optical sensor, or other devices configured to survey and measure an environment around the subject of the data gathering or imaging, the subject being, for example, a patient or another object being tracked in the environment. Environmental sensor 104 may have a connection 108 that is wired or unwired. In an embodiment, display device 103 may be configured with integrated environmental sensor 104.

In an embodiment, universal streaming device 101 and display device 103 are configured to integrate the environment being viewed by a user, using a wearable device, with data being collected by the data source equipment 102. Display device 103 is configured to allow the user to clearly view the subject, i.e., the patient, while data and images are displayed to the user via the wearable device. Thus, the user can view biometric data and images overlaid as if they are within or penetrating into a subject while also concurrently viewing the patient externally.

In an embodiment, the display device 103 may be configured to project an image. The display device 103 may be configured to project the image onto a surface within the viewing field of the user. For example, the display device may receive data from data source equipment 102 and environmental sensor 104 to recognize the direction of gaze of the user and project data or images onto a surface in the direction of gaze. For example, the display device 103 may be configured to direct a projection onto a wall, a floor, or elsewhere as appropriate. In an embodiment, the display device 103 may be configured to project an image onto the body of the subject being examined or about which data is being gathered.

In an embodiment, display device 103 may be configured to display data and images visible only to the wearer of the wearable device. Such a wearable device may be embodied as a pair of transparent lenses or other optical device. For example, in an embodiment, the display device 103 is configured to superimpose data or images (or both) on an inner surface of a wearable device such that the user of the wearable device is able to view the surrounding environment with the data or images overlaid on the surrounding environment visible through the wearable device.

In an embodiment, system 100 may be configured to receive input from a human-computer interface (HCI) through HCI input port 109 which may be wired or wireless. Such HCI may include a keyboard and mouse, a touch pad, or any other type of HCI. In an embodiment, display device 103 may be configured with an HCI allowing for interpretation of various user commands. These commands may include, but are not limited to, hand gestures, voice commands, and/or eye tracking. In such an embodiment, a user may be able to directly control various parameters of system 100 using commands submitted through display device 103.

Additionally, in an embodiment, data source equipment 102 may have a port 106 configured to accept data input into data source equipment 102. Port 106 may be a distinct and separate port from port 105. In an embodiment, port 106 may be a common port with port 105. Port 106 may be configured to accept data that may include control commands for the data source equipment 102. In an embodiment, HCI input may be passed to data source equipment 102 via universal streaming device 101 utilizing HCI input port 109 and port 106. In such an embodiment, display device 103 may be used as an HCI to control various data acquisition parameters within data source equipment 102.

Figure 2:
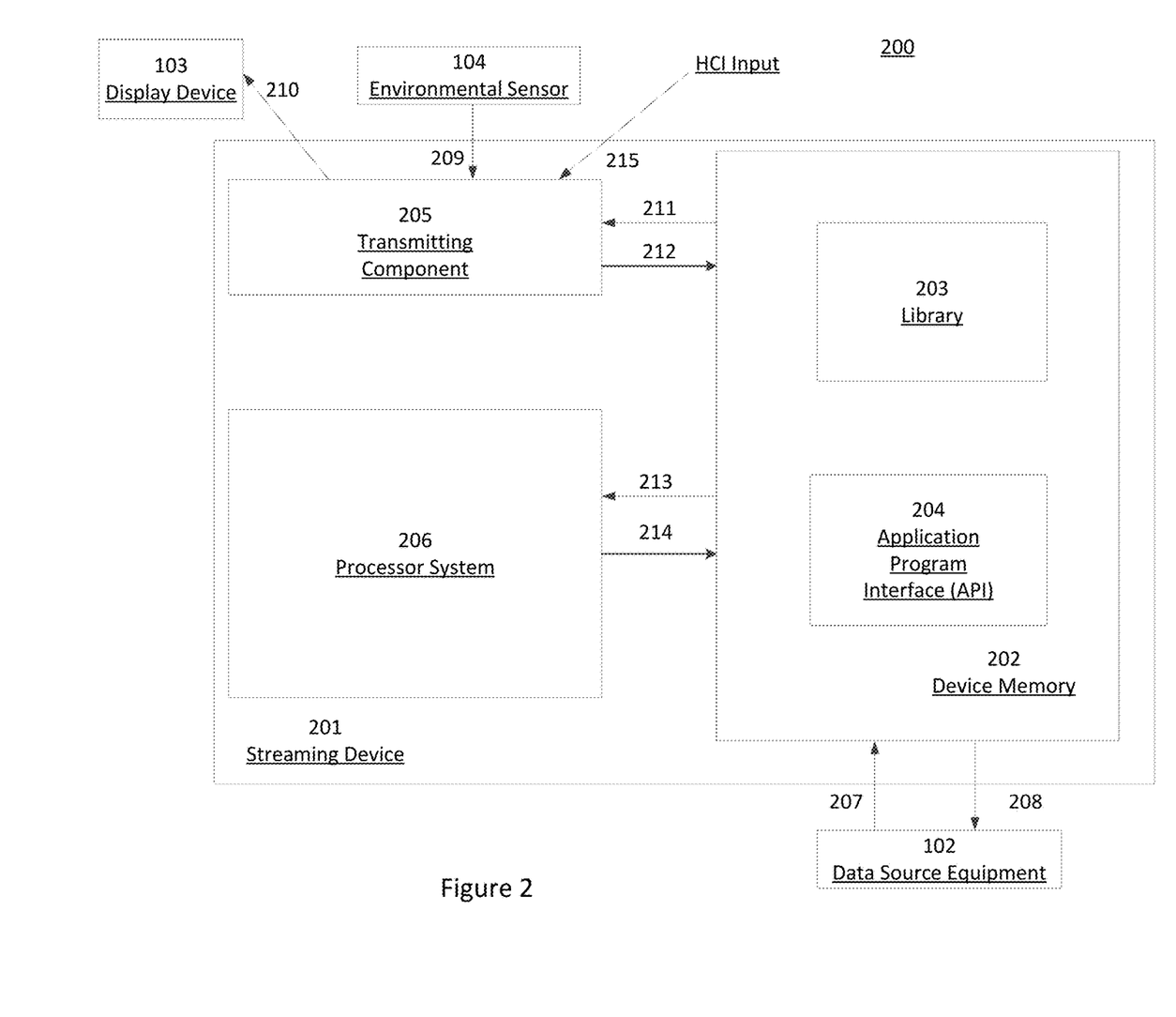
FIG. 2 illustrates a flowchart of components of a device according to an example embodiment.

FIG. 2 illustrates a flowchart of components of universal streaming device 101 according to an example embodiment.

As shown in FIG. 2, a system 200 including a streaming device 201 is depicted. The streaming device 201 may be configured to include a device memory 202. In an embodiment, device memory 202 may include a library 203 of APIs which may be configured to control data source equipment 102 like those described above. Device memory 202 of streaming device 201 may also include an API 204 configured to allow input of various sensor data. API 204 may be configured to allow input of various HCI commands. In an embodiment, streaming device 201 may include transmitting component 205. In an embodiment, transmitting component 205 may be configured as a wired transmitting component. In an embodiment, transmitting component 205 may be configured as a wireless transmitting component.

In an embodiment, streaming device 201 may include a processor system 206 which may be a microprocessor system. Processor system 206 may include components, including a CPU, GPU, ASICS, and other components as appropriate. In an embodiment, device memory 202 may be configured to receive data from data source equipment 102 via connection 207. In an embodiment, device memory 202 may be configured to transmit data to data source equipment 102 via connection 208.

In an embodiment, transmitting component 205 may be configured to receive data from environmental sensor 104 via connection 209. In an embodiment, transmitting component 205 may be configured to transmit data to display device 103 via connection 210. In an embodiment, transmitting component 205 may be configured to receive HCI input data via connection 215. Additionally, transmitting component 205 may be connected to device memory 202 by input and output connections 211, 212. Processor system 206 may be connected to device memory 202 by input and output connections 213, 214.

Figure 3:
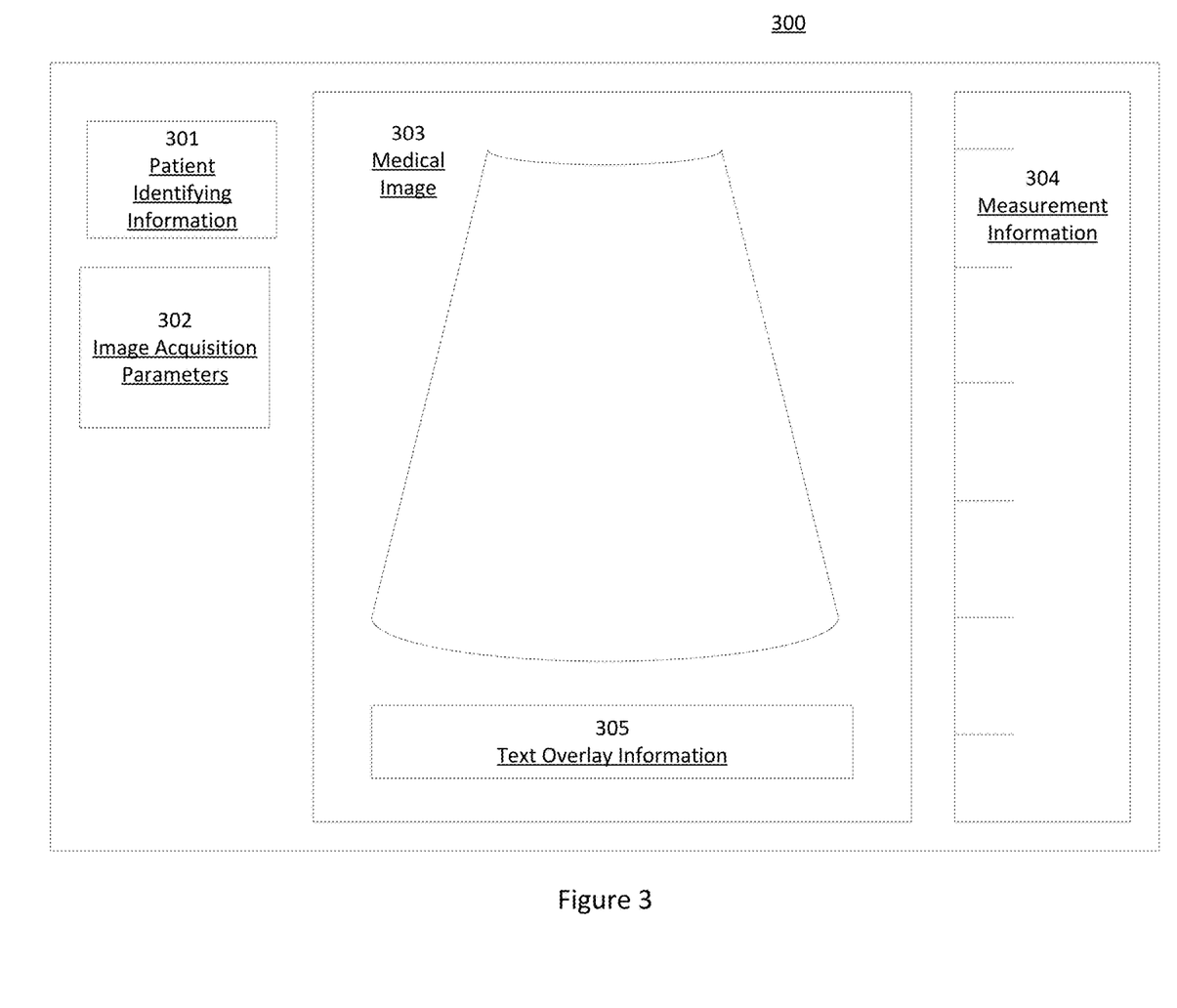
FIG. 3 is an illustration of an example captured image frame with various data points according to an example embodiment.

FIG. 3 is an illustration of an example captured image frame 300 with various data points according to an example embodiment.

As shown in FIG. 3, an example captured image frame may contain various data points that universal streaming device 101 may be configured to extract. An OCR or computer vision algorithm may identify and extract patient identifying information 301, image acquisition parameters 302, measurement information 304, or other text overlay information 305. In an embodiment, universal streaming device 101 may also be configured with computer vision algorithms allowing for computer aided detection (CAD) of medical images 303.

Figure 4:
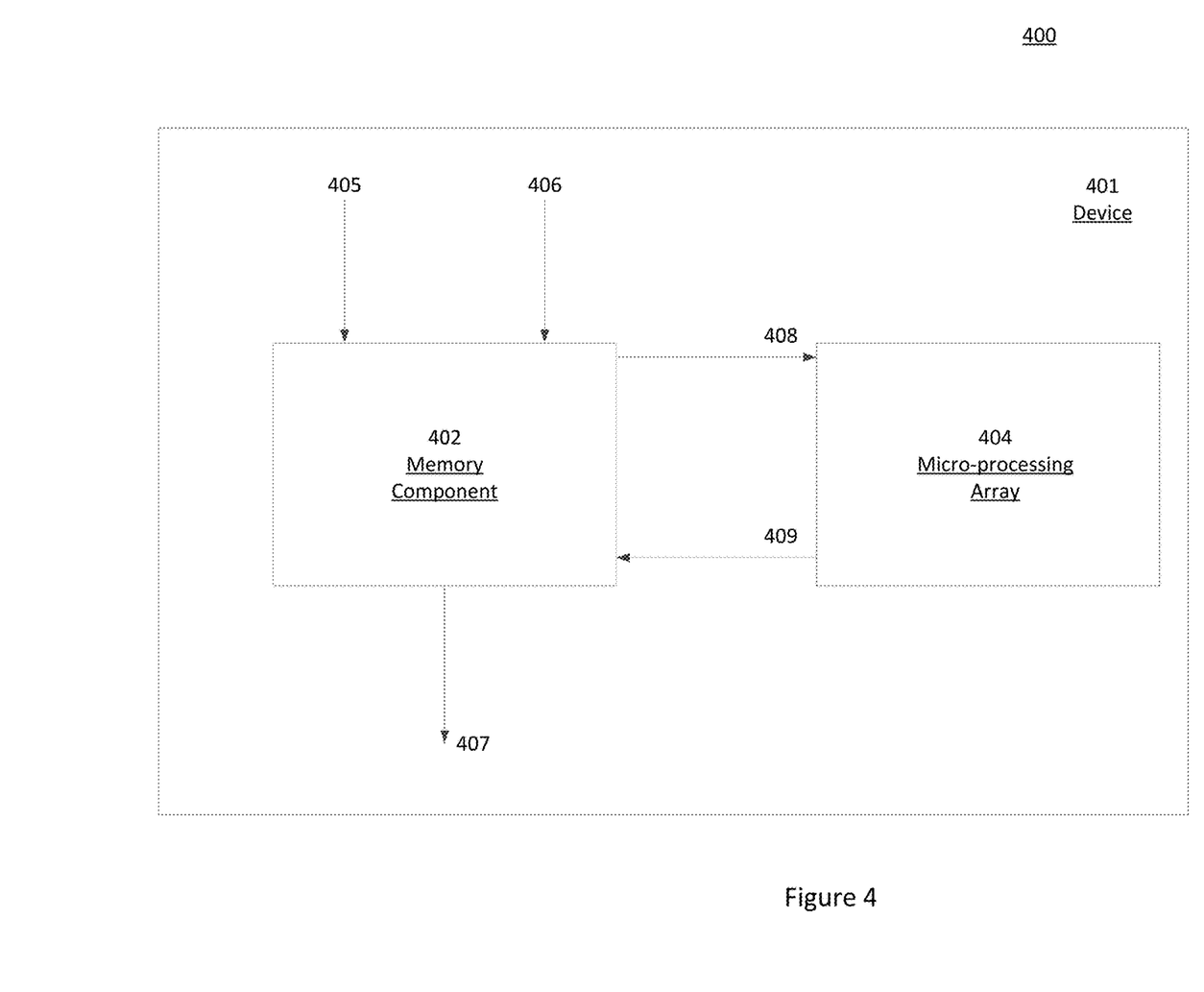
FIG. 4 is an illustration of sensor data input and modification of capture data according to an example embodiment.

FIG. 4 is an illustration of sensor data input and modification of capture data according to an example embodiment.

As shown in FIG. 4, a system 400 for data capture is depicted. In an embodiment, memory component 402 may be configured to store source data provided to the memory component 402 via input 405. In an embodiment, memory component 402 may be configured to store environmental data provided to the memory component 402 via connection 406. Memory component 402 may also have an output 407 configured to export data which may be raw or modified. Memory component 402 may include an output 407 through which data may be sent to an output device to make data and images available to a user of system 400.

Figure 5:
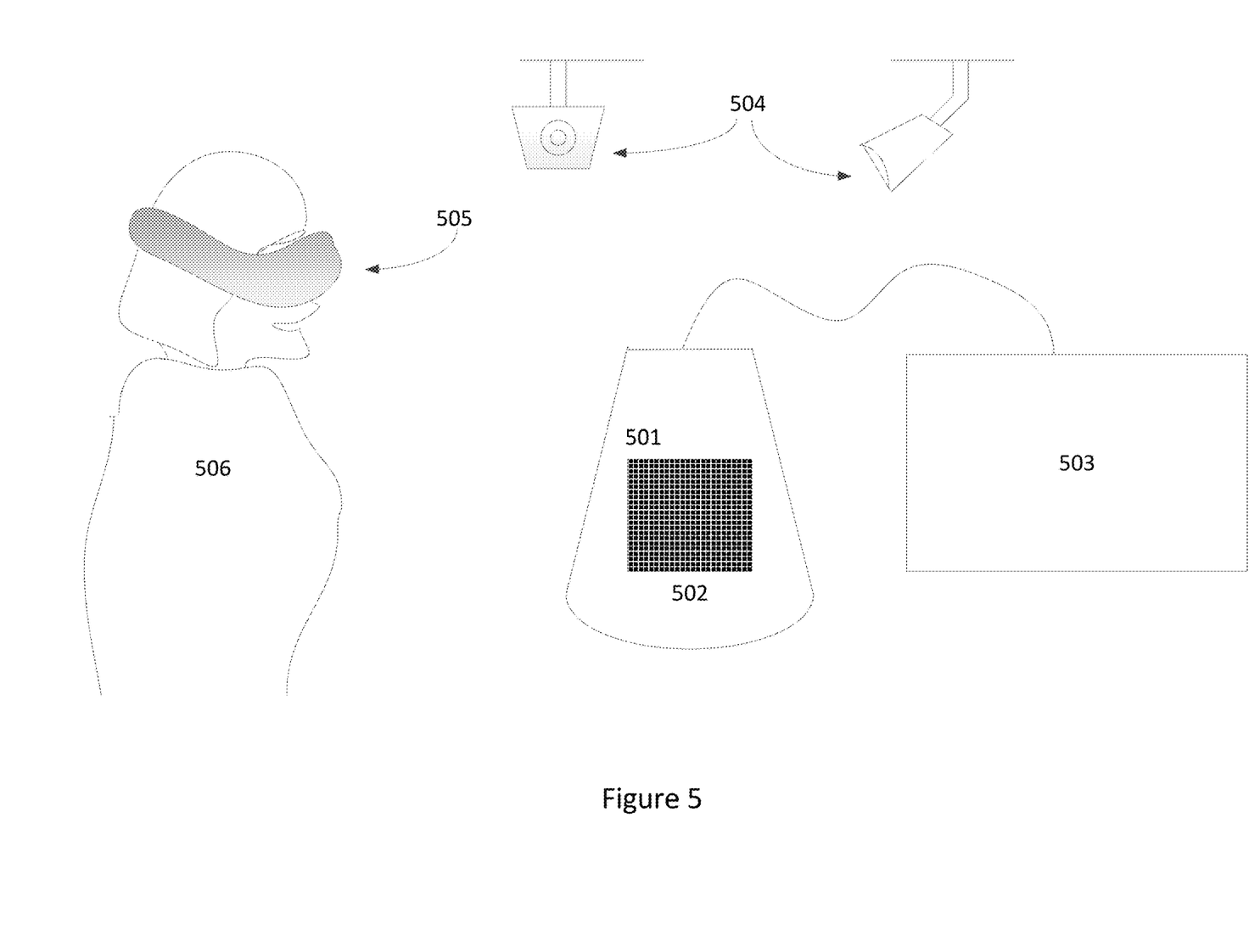
FIG. 5 is an illustration of environmental tracking using a fiducial marker according to an example embodiment.

In an embodiment, memory component 402 may additionally be connected through an output 408 and an input 409 to a micro-processing array 404 including components configured to ensure data is transmitted appropriately and with low latency. In an embodiment, micro-processing array 404 may include components to analyze data coming into memory component 402 from input 405 and connection 406. Micro-processing array 404 may analyze and interpret data input into memory component 402 such that the device 401 may provide contextualized output to a user through output 407. Micro-processing array may include at least a first API to modify data input into device 401 such that data output to a user via output 407 is appropriately contextualized for the environment and situation facing the user using the device 401. FIG. 5 is an example illustration demonstrating environmental and element tracking according to an example embodiment. As shown in FIG. 5, a tracking element 501 may be affixed to a trackable component 502 of data source equipment 503. This tracking element, or a fiducial marker, may be tracked with external environmental sensors 504 or with sensors embedded in a display device 505 which may be worn by a professional 506.

Figure 6:
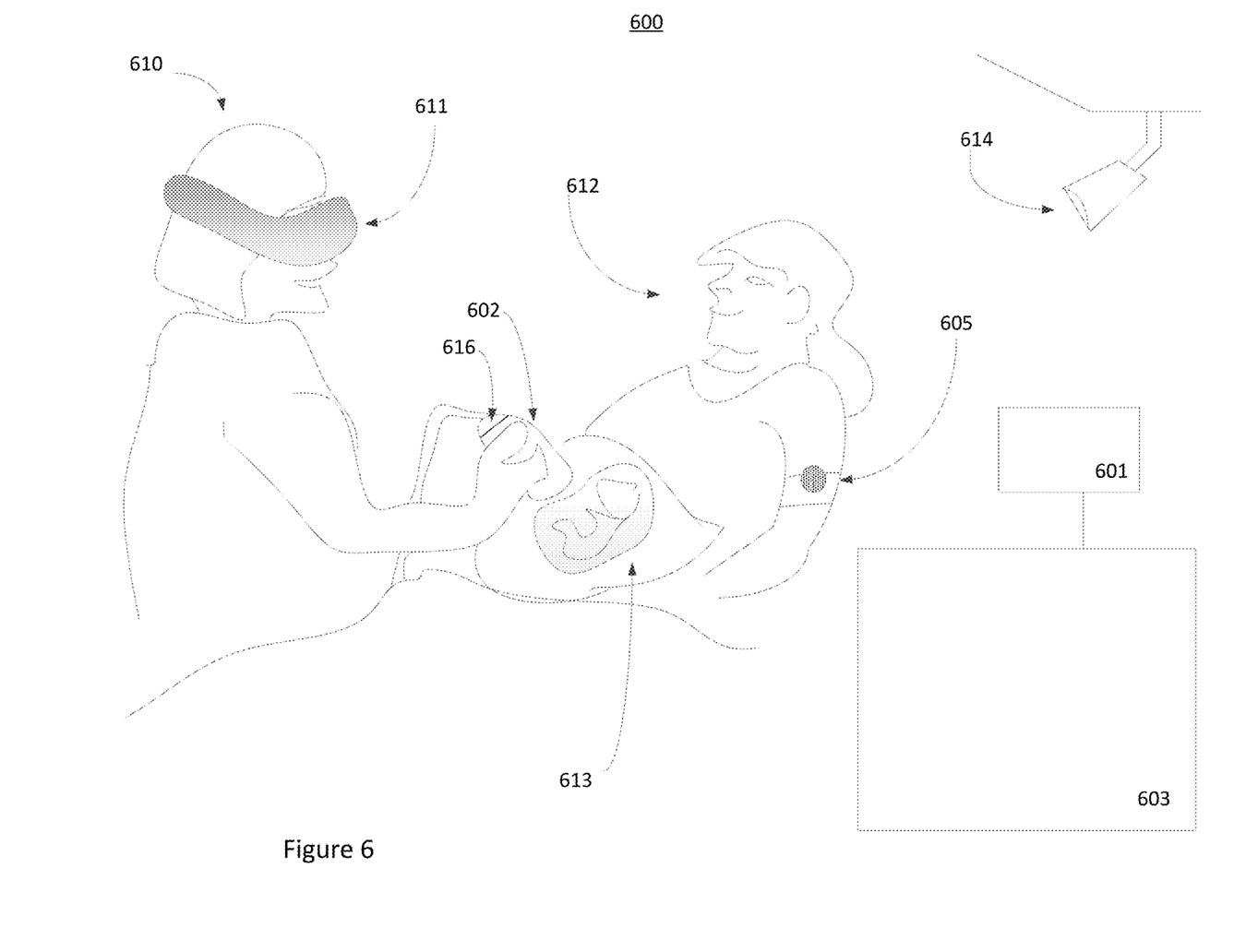
FIG. 6 is an illustration of a professional using an embodiment of the system according to an example embodiment.

FIG. 6 is an illustration of a professional using an embodiment of the system according to an example embodiment.

As shown in FIG. 6, a system 600 whereby a medical professional or other user 610 handling a piece of data source equipment 602 with a trackable element 616, embodied here as an ultrasound device, is depicted. Data source equipment 602 is connected to computer components 603, which may include a processor, bus, memory, and an algorithm such as an API. Computer components 603 may be connected to a display such as a computer monitor. User 610 may also use a wearable device 611. Data captured by device 601 from computer components 603 may be transmitted to display device 611 as modified or unmodified data. Data may be modified as to be displayed in a contextually appropriate manner utilizing environmental sensor 614 data as well as data points extracted from captured data, for example as outlined by FIG. 3. In an embodiment, a trackable element 605 may provide data which may be incorporated by computer components 603 and may be displayed to user 610. Trackable element 605 may be embodied as a wearable element (as illustrated), a sensor, or incorporated as part of data source equipment 602. In this manner, user 610 may view contextualized or contextually modified source images provided by the device 601 according to an embodiment of the invention. Contextually modified images and contextually modified source images can contain text, icons, graphics or any other image type. An image is not meant to be limiting in any manner.

In an embodiment, wearable device 611 displays within the wearable device 611 the contextualized images for the user 610 to view. In another embodiment, the wearable device 611 may broadcast or project the contextualized images onto a surface, including the patient 612, illustrated as image 613.

In an alternate embodiment, user 610 may control an image projecting device, which may be handheld or wearable, such that the image is projected onto the surface or patient 612 such that anyone in the viewing vicinity is able to view the images 613.

Figure 7:
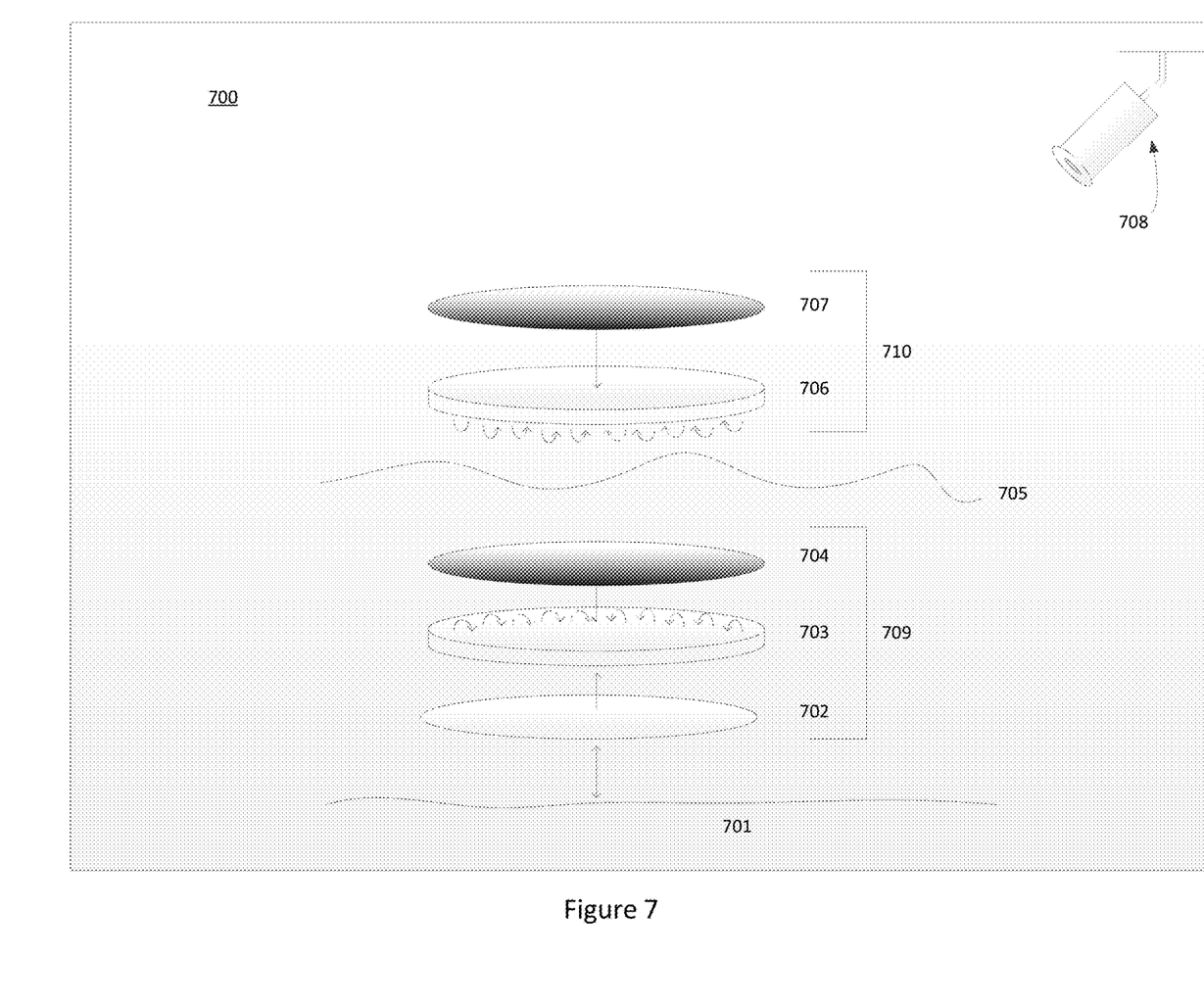
FIG. 7 is an illustration of a magnetic based self-aligning fiducial marker system according to an example embodiment.

FIG. 7 is an illustration of a magnetic based self-aligning fiducial marker system according to an example embodiment.

As shown in FIG. 7, a system 700 for correlating trackable fiducial markers before and after field sterilization during image guided procedures may be utilized. In an embodiment, a non-sterile magnet 703 has an adhesive backing 702 which allows the non-sterile magnet to be affixed to a patient 701. The non-sterile magnet may have a non-sterile trackable identifier 705 affixed to the complimentary magnetic surface. As such, the non-sterile fiducial assembly 709 may encompass an assembly of components such as an adhesive backing 702, a non-sterile magnet 703, and a drape 704. Prior to patient sterilization, environmental sensor 708 may track non-sterile fiducial assembly 709. Subsequent to patient sterilization a drape 704 may be overlaid on the patient and may cover the non-sterile fiducial assembly 709 preventing direct tracking by environmental sensor 708.

A sterile fiducial assembly 710 includes an assembly of a sterile magnet 706 which has complimentary attractive forces and properties allowing for accurate alignment with non-sterile magnet 703. Sterile magnet 706 may have a sterile trackable marker 707 on its non-complementary magnetic surface which can be tracked by environmental sensor 708. With a drape covering the non-sterile fiducial assembly 709, sterile fiducial assembly 710 can be overlaid and accurately aligned to 709 using intrinsic magnetic properties.

Figure 8:
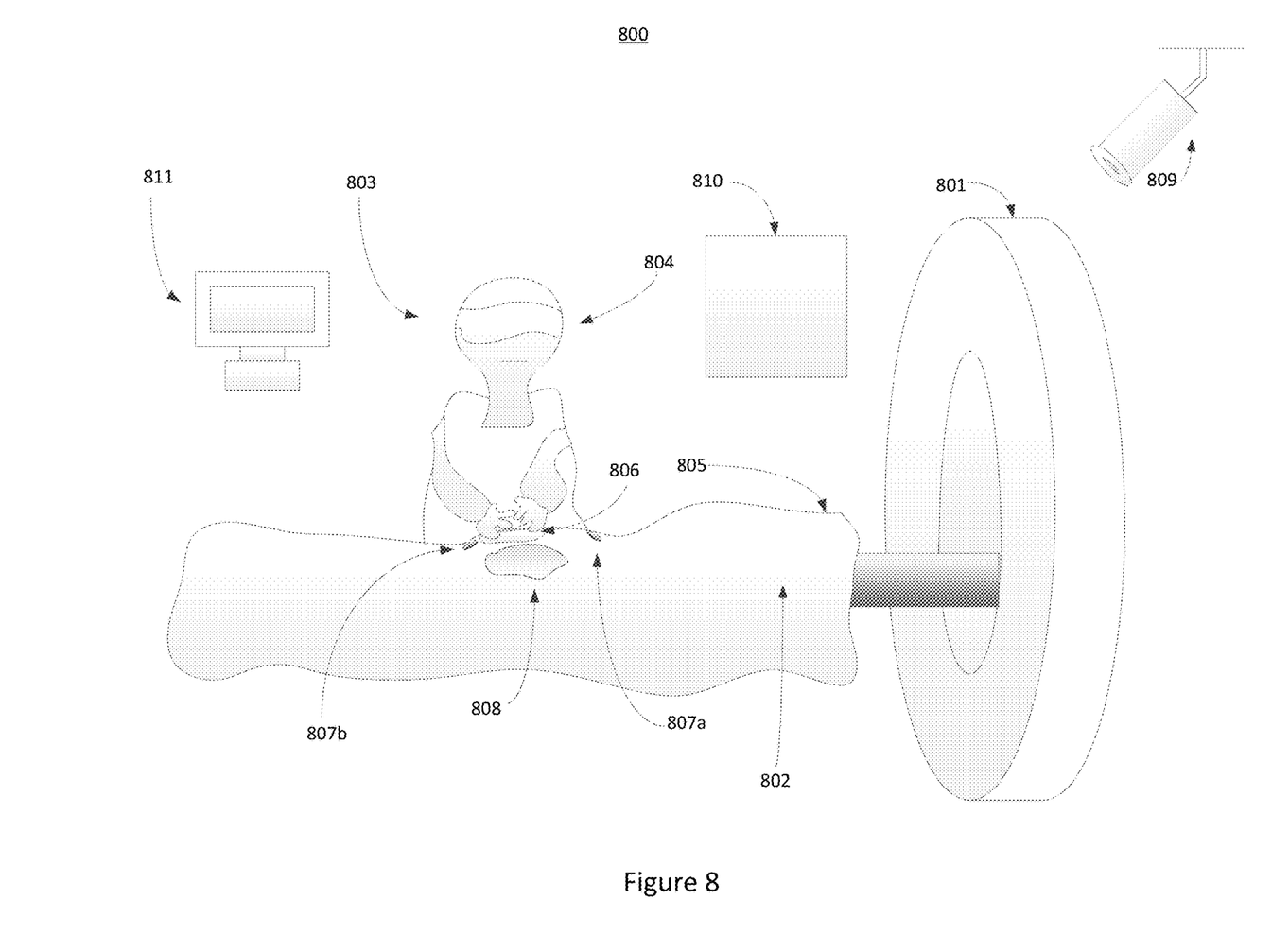
FIG. 8 is an illustration of a professional using an embodiment of the system with a self-aligning fiducial marker according to an example embodiment.

FIG. 8 is an illustration of a professional using an embodiment of the system with a self-aligning fiducial marker system according to an example embodiment.

As shown in FIG. 8, a system 800 whereby a medical professional or other user 803 is using data source equipment 801, illustrated by a CT scan in an embodiment, to perform an image guided procedure on patient 802. In this example, user 803 is working in patient sterile region 806 concerning a patient structure 808 while a sterile drape 805 overlies the patient 802. Two fiducial markers 807*a* and 807*b* that are trackable and similar to those depicted in FIG. 7, are in place within the sterile field. External sensor 809 may track fiducial markers 807*a* and 807*b*. In an embodiment, a wearable display device 804 may also contain at least a first external sensor, the additional sensor allowing for tracking of fiducial markers 807*a* and 807*b*. In an embodiment, regional topographic and texture features adjacent to fiducial markers 807*a* and 807*b* may expand the trackable region as sensed by external sensor 809.

Data source equipment 801 may be connected to computer components 810, which may include a processor, bus, memory, and an algorithm such as an API. Computer components 810 may be connected to a display such as a computer monitor. User 803 may also use a wearable display device 804. Data captured by computer components 810 from data source equipment 801 may be transmitted to display device 811 or wearable device 804 as modified or unmodified data. Data may be modified as to be displayed in a contextually appropriate manner utilizing external sensor 809 while tracking any number of fiducial markers such as 807*a*, 807*b*, both, or additional added markers. In an embodiment data may be modified from data captured by computer components 810, for example as outlined by FIG. 3, or embedded metadata within source imaging data, e.g., source images, derived from 801. In this manner, user 803 may view contextualized or contextually modified images provided by data source equipment 801 according to an embodiment of the invention.

The various embodiments discussed herein may be used to capture and display a variety of data, including medical images such as CT, ultrasound, MRI, fluoroscopy, angiography, and optical fibroscopic images such as those imaged during laparascopy, colonoscopy, endoscopic gastroduodenoscopies (EGD), and cystoscopy, among others. Data may include images as well as vitals such as blood pressure, heart rate, respiratory rate, pulse oxygenation, temperature, and other biometric readings. The data may also include electrocardiography (EKG), electroencephalography (EEG), electromyography, and other such data. Further, an embodiment may include settings and data parameters of various life support systems such as ventilators, dialysis machines, extracorporal membrane oxygenation (ECMO) machines, and others. In an embodiment, data may also include and incorporate laboratory, pathology, and microbiology data that may be stored otherwise in electronic medical records.

The system described herein may be useful during surgical procedures to provide medical professionals with real-time or near real readouts of vital information and images during medical procedures. Some such surgical procedures may include fibroscopic assisted procedures including laparoscopy, cystoscopy, bronchoscopy, colonoscopy, endoscopy, and laryngoscopy, among others. Some other surgical procedures may include ultrasound or other fluoroscopic interventions such as liver, kidney, bone, or other biopsies, venous or arterial catheter placement, angiography, genitourinary interventions, orthopedics, ophthalmological interventions, hepatobiliary interventions, neurological interventions, and other procedures.

The wearable device may be embodied as a system of wearable devices, which may include a plurality of wearable components, the plurality of wearable components allowing the user of the system to both view data and images, as well as to control the devices collecting data. The plurality of wearable components may include components which interpret gestures to control which data and images are displayed. In an embodiment, the wearable components may be configured to interpret gestures to control the data collection device.

One having ordinary skill in the art will readily understand that the invention as discussed above may be practiced with steps in a different order, and/or with elements in configurations that are different than those which are disclosed. Therefore, although the invention has been described based upon these preferred embodiments, it would be apparent to those of skill in the art that certain modifications, variations, and alternative constructions would be apparent, while remaining within the spirit and scope of the invention.

We claim:

1. A system for integrated diagnostic testing and real-time treatment comprising:
   a medical data gathering device configured to capture a plurality of source images, wherein at least one of the source images contains a fiducial marker;
   a low latency encoder configured to encode the plurality of source images into a data stream;
   an environmental sensor device configured to capture sensor data;
   a processor configured to contextually modify at least one of the source images based on the sensor data and the fiducial marker; and
   a transmitting device configured to transmit contextually modified source images to a wearable display device that displays the contextually modified source images on anatomically correct locations of a patient to illustrate a path for a biopsy device.

2. The system of claim 1, wherein the data stream is configured for secure wireless transmission.

3. The system of claim 1, wherein the medical data gathering device includes an ultrasound imaging device.

4. The system of claim 1, wherein the medical data gathering device comprises an imaging device configured to provide noninvasive imagery from within a patient.

5. The system of claim 1, wherein the processor further modifies source images based on input from the wearable display device.

6. The system of claim 1, wherein contextual modification of the source images is performed in real-time.

7. The system of claim 1, wherein the environmental sensor is configured to track a direction of gaze of a user.

8. A method for integrated diagnostic testing and real-time treatment comprising:
   capturing a plurality of medical source images, wherein at least one of the medical source images contains a fiducial marker;
   encoding the plurality of medical source images into a data stream using a low latency encoder;
   capturing environmental sensor data;
   contextually modifying at least one of the medical source images based on the environmental sensor data and the fiducial marker; and
   transmitting at least one of the contextually modified medical source images to a wearable display device that displays the contextually modified source images on anatomically correct locations of a patient to illustrate a path for a biopsy device.

9. The method of claim 8, wherein the data stream is configured for secure wireless transmission.

10. The method of claim 8, wherein the capturing of the plurality of medical source images is performed using an ultrasound imaging device.

11. The method of claim 8, wherein the capturing of the plurality of medical source images is performed using a non-invasive medical data gathering device.

12. The method of claim 8, further comprising modifying at least one of the medical source images based on input from the wearable display device.

13. The method of claim 8, wherein contextual modification of at least one of the medical source images is performed in real-time.

14. The method of claim 8, wherein an environmental sensor is configured to track a direction of gaze of a user.

15. A non-transitory computer readable medium with instructions stored thereon for integrated diagnostic testing and real-time treatment, the testing and treatment comprising:
   capturing a plurality of medical source images using an ultrasound imaging device, wherein at least one of the medical source images contains a fiducial marker;
   encoding the plurality of medical source images into a data stream using a low latency encoder;
   capturing environmental sensor data;
   contextually modifying at least one of the medical source images based on the environmental sensor data and the fiducial marker; and
   transmitting at least one of the contextually modified medical source images to a wearable display device that displays the contextually modified source images on anatomically correct locations of a patient to illustrate a path for a biopsy device.

16. The non-transitory computer readable medium of claim 15, wherein the data stream is configured for secure wireless transmission.

17. The non-transitory computer readable medium of claim 15, wherein the capturing of the plurality of medical source images is performed with a medical tool that provides noninvasive imagery from within a patient.

18. The non-transitory computer readable medium of claim 15, further comprising modifying at least one of the medical source images based on input from the wearable display device.

19. The non-transitory computer readable medium of claim 15, wherein contextual modification of at least one of the medical source images is performed in real-time.

20. The non-transitory computer readable medium of claim 15, wherein an environmental sensor is configured to track a direction of gaze of a user.

* * * * *